US011351179B1

(12) United States Patent
Wang et al.

(10) Patent No.: US 11,351,179 B1
(45) Date of Patent: Jun. 7, 2022

(54) PHARMACEUTICAL COMPOSITIONS AND METHODS FOR TREATMENT OF PSYCHIATRIC DISORDERS

(71) Applicant: LA PharmaTech Inc., Blacksburg, VA (US)

(72) Inventors: Jianmin Wang, Blacksburg, VA (US); Geping Cui, Beijing (CN)

(73) Assignee: LA PharmaTech Inc., Blacksburg, VA (US)

( * ) Notice: Subject to any disclaimer, the term of this patent is extended or adjusted under 35 U.S.C. 154(b) by 0 days.

(21) Appl. No.: 17/394,898

(22) Filed: Aug. 5, 2021

(51) Int. Cl.
*A61K 31/55* (2006.01)
*A61P 25/22* (2006.01)
*A61P 25/24* (2006.01)
*A61K 31/519* (2006.01)

(52) U.S. Cl.
CPC ............ *A61K 31/55* (2013.01); *A61K 31/519* (2013.01); *A61P 25/22* (2018.01); *A61P 25/24* (2018.01)

(58) Field of Classification Search
CPC ....... A61K 31/55; A61K 31/519; A61P 25/22; A61P 25/24
See application file for complete search history.

(56) References Cited

U.S. PATENT DOCUMENTS

| | | | |
|---|---|---|---|
| 5,068,233 A | 11/1991 | Achterrath-Tuckerman et al. |
| 5,086,050 A | 2/1992 | Hettche et al. |
| 5,110,814 A | 5/1992 | Engel et al. |
| 5,994,357 A | 11/1999 | Theoharides |
| 6,008,221 A | 12/1999 | Smith et al. |
| 6,017,909 A | 1/2000 | Hettche et al. |
| 6,191,133 B1 | 2/2001 | Coppen |
| 6,200,607 B1 | 3/2001 | Bridgeman |
| 6,849,621 B2 | 2/2005 | Rosenblum et al. |
| 7,022,687 B1 | 4/2006 | Szelenyi et al. |
| 7,220,735 B2 | 5/2007 | Ting et al. |
| 7,355,042 B2 | 4/2008 | Edgar et al. |
| 7,384,981 B2 | 6/2008 | Kiliaan et al. |
| 7,615,550 B2 | 11/2009 | Heightman et al. |
| 7,786,161 B2 | 8/2010 | Tani et al. |
| 7,888,391 B2 | 2/2011 | Kiliaan et al. |
| 8,071,073 B2 | 12/2011 | Dang et al. |
| 8,168,620 B2 | 5/2012 | Lulla et al. |
| 8,304,405 B2 | 11/2012 | Lulla et al. |
| 8,318,709 B2 | 11/2012 | Lulla et al. |
| 8,362,078 B2 | 1/2013 | Kiliaan et al. |
| 8,372,451 B2 | 2/2013 | Vuckovic |
| 8,440,243 B2 | 5/2013 | Maewal |
| 8,741,319 B2 | 6/2014 | Crain et al. |
| 8,758,816 B2 | 6/2014 | Fuge et al. |
| 8,859,531 B2 | 10/2014 | Lee et al. |
| 8,865,733 B2 | 10/2014 | Felder |
| 9,278,092 B2 | 3/2016 | Chase et al. |
| 9,308,223 B2 | 4/2016 | Maewal |
| 9,504,712 B2 | 11/2016 | Kiliaan et al. |
| 9,662,359 B2 | 5/2017 | Vuckovic |
| 9,844,525 B2 | 12/2017 | Kiliaan et al. |
| 9,901,585 B2 | 2/2018 | Lulla et al. |
| 9,919,050 B2 | 3/2018 | Dang et al. |
| 10,639,314 B1 | 5/2020 | Wang et al. |
| 10,639,315 B1 | 5/2020 | Wang et al. |
| 10,639,316 B1 | 5/2020 | Wang et al. |
| 10,898,493 B2 | 1/2021 | Wang et al. |
| 10,946,026 B2 | 3/2021 | Wang et al. |
| 10,966,989 B2 | 4/2021 | Wang et al. |
| 11,116,773 B2 | 9/2021 | Wang et al. |
| 2003/0229030 A1* | 12/2003 | Theoharides ........ A61K 31/353 514/27 |
| 2005/0163843 A1 | 7/2005 | Boehm et al. |
| 2006/0051416 A1 | 3/2006 | Rastogi et al. |
| 2009/0318703 A1 | 12/2009 | Tani et al. |
| 2010/0152108 A1 | 6/2010 | Hung et al. |
| 2012/0237570 A1 | 9/2012 | Crain et al. |
| 2013/0252929 A1 | 9/2013 | Lee et al. |
| 2014/0127328 A1 | 5/2014 | Crain et al. |
| 2014/0158117 A1 | 6/2014 | Dang et al. |
| 2015/0216849 A1 | 8/2015 | Dedhiya et al. |

(Continued)

FOREIGN PATENT DOCUMENTS

AU 2019443520 A1 12/2021
AU 2019445048 A1 12/2021

(Continued)

OTHER PUBLICATIONS (Wang, Jianmin) Co-Pending U.S. Appl. No. 16/382,885, filed Apr. 12, 2019, Specification and claims.
(Wang, Jianmin) Co-Pending U.S. Appl. No. 16/398,845, filed Apr. 30, 2019, Specification and Claims.
(Wang, Jianmin) Co-Pending U.S. Appl. No. 16/418,614, filed May 21, 2019, Specification and Claims.
(Wang, Jianmin) Co-pending U.S. Appl. No. 16/424,788, filed May 29, 2019, Specification and Claims.
(Wang, Jianmin) Co-Pending U.S. Appl. No. 16/426,121, filed May 30, 2019, Specification and Claims.
(Wang, Jianmin) Co-Pending U.S. Appl. No. 16/831,330, filed Mar. 26, 2020, Specification and Claims.
(Wang, Jianmin) Co-Pending U.S. Appl. No. 16/834,146, filed Mar. 30, 2020, Specification and Claims.
(Wang, Jianmin) Co-Pending U.S. Appl. No. 16/884,459, filed May 27, 2020, Specification and Claims.

(Continued)

*Primary Examiner* — Sahar Javanmard
(74) *Attorney, Agent, or Firm* — New River Valley IP Law, P.C.; Michele L. Mayberry

(57) ABSTRACT

Pharmaceutical compositions comprising azelastine or a pharmaceutically acceptable salt of azelastine and folic acid or folate, and/or salts, metabolites, or derivatives thereof are disclosed. Methods of using the pharmaceutical compositions for treating patients suffering from one or more psychiatric disorders or symptoms, such as major depressive disorder, generalized anxiety disorder, panic disorder, agitation, social anxiety disorder, mild chronic depression, obsessive-compulsive disorder, premenstrual dysphoric disorder, seasonal affective disorder, dysthymia, bipolar disorder, posttraumatic stress disorder, sleep disorder related to anxiety, are also disclosed.

19 Claims, No Drawings

(56) References Cited

U.S. PATENT DOCUMENTS

| | | |
|---|---|---|
| 2017/0035780 A1 | 2/2017 | Lulla et al. |
| 2018/0104294 A1 | 4/2018 | Vuckovic |
| 2018/0116979 A1 | 5/2018 | Clarence-Smith et al. |
| 2020/0323867 A1 | 10/2020 | Wang et al. |
| 2020/0323868 A1 | 10/2020 | Wang et al. |
| 2020/0323870 A1 | 10/2020 | Wang et al. |
| 2020/0323871 A1 | 10/2020 | Wang et al. |
| 2020/0323873 A1 | 10/2020 | Wang et al. |
| 2020/0323876 A1 | 10/2020 | Wang et al. |
| 2020/0323877 A1 | 10/2020 | Wang et al. |
| 2021/0069209 A1 | 3/2021 | Wang et al. |
| 2022/0000882 A1 | 1/2022 | Wang et al. |

FOREIGN PATENT DOCUMENTS

| | | |
|---|---|---|
| AU | 2019446955 A1 | 12/2021 |
| CA | 3136633 A1 | 10/2020 |
| CA | 3137393 A1 | 11/2020 |
| CA | 3139082 A1 | 11/2020 |
| CN | 113924098 A | 1/2022 |
| CN | 113939276 A | 1/2022 |
| CN | 114072945 A | 2/2022 |
| EP | 3952840 A1 | 2/2022 |
| EP | 3962488 A1 | 3/2022 |
| WO | 2006058022 A1 | 6/2006 |
| WO | 2007061454 A1 | 5/2007 |
| WO | 2014018563 A3 | 5/2014 |
| WO | 2017151723 A1 | 9/2017 |
| WO | 2020209872 A1 | 10/2020 |
| WO | 2020222799 A1 | 11/2020 |
| WO | 2020236159 A1 | 11/2020 |
| WO | 2021242235 A1 | 12/2021 |
| WO | 2021242297 A1 | 12/2021 |
| WO | 2021262196 A1 | 12/2021 |

OTHER PUBLICATIONS (Wang, Jianmin) Co-Pending U.S. Appl. No. 16/884,553, filed May 27, 2020, Specification and Claims.
(Wang, Jianmin) Co-Pending U.S. Appl. No. 16/913,927, filed Jun. 26, 2020, Specification and Claims.
(Wang, Jianmin) Co-Pending U.S. Appl. No. 17/094,405, filed Nov. 10, 2020, Specification and Claims.
(Wang, Jianmin) Co-Pending U.S. Appl. No. 17/459,868, filed Aug. 27, 2021, Specification and Claims.
(Wang, Jianmin) Co-Pending Application No. PCT/US19/27293, filed Apr. 12, 2019, Specification and Claims.
(Wang, Jianmin) Co-Pending Application No. PCT/US19/29885, Filed Apr. 30, 2019, Specification and Claims.
(Wang, Jianmin) Co-Pending Application No. PCT/US19/33359, Filed May 21, 2019, Specification and Claims.
(Wang, Jianmin) Co-Pending Application No. PCT/US20/34735, filed May 27, 2020, Specification and Claims.
(Wang, Jianmin) Co-Pending Application No. PCT/US20/39916, Filed Jun. 26, 2020, Specification and Claims.
(Wang, Jianmin) Co-Pending Application No. PCT/US20/59846, filed Nov. 10, 2020, Specification and claims.
(Wang, Jianmin) Co-Pending Application No. PCT/US21/44654, filed Aug. 5, 2021, Specification and Claims.
Balashova, Olga A. et al. "Folate Action in Nervous System Development and Disease", Dev Neurobiol. Apr. 2018;78(4): 391-402.
Bennett, F. C. and Molofsky, A. V., "The immune system and psychiatric disease: a basic science perspective", Clinical and Experimental Immunology, 197: 291-307.
Bezprozvanny, Ilya. The rise and fall of Dimebon. National Institute of Health. Feb. 12, 2014.
Bottiglieri, Teodoro et al. "Homocysteine, folate, methylation, and monoamine metabolism in depression", J Neurol Neurosurg Psychiatry 2000; 69:228-232.
Casale, T. B. The interaction of azelastine with human lung histamine H1, beta, and muscarinic receptor-binding sites. J Allergy Clin Immunol. 1989;83:771-776.
Category H1 receptor antagonists. Wikipedia. Sep. 20, 2012.
Catena-Dell'Osso, M. et al., 2011, Inflammatory and Neurodegenerative Pathways in Depression: A New Avenue for Antidepressant Development? Curr Med Chem. 18 (2), 245-55, Abstract, 2 pages.
Ciprandi, G., Pronzato, C., Passalacqua, G., et al. Topical azelastine reduces eosinophil activation and Intercellular adhesion molecule-1 expression on nasal epithelial cells: An antiallergic activity. J Allergy Clin Immunol. 1996;98(6 Pt 1):1088-1096.
Conti, Pio et al., "Impact of Mast Cells in Depression Disorder: Inhibitory Effect of IL-37 (New Frontiers)". Immunol Res, vol. 66 (3), 323-331 Jun. 2018.
Co-Pending U.S. Appl. No. 16/382,885, Final office action dated Jun. 5, 2020, 13 pgs.
Co-Pending U.S. Appl. No. 16/382,885, Non-Final office action and list of references dated Nov. 29, 2019, 23 pgs.
Co-Pending U.S. Appl. No. 16/382,885, Non-Final office action dated Dec. 22, 2020, 19 pgs.
Co-Pending U.S. Appl. No. 16/382,885, Notice of Allowance dated Feb. 10, 2021, 9 pages.
Co-Pending U.S. Appl. No. 16/382,885, Response to Dec. 22, 2020 Non-Final office action filed Jan. 21, 2021, 7 pgs.
Co-Pending U.S. Appl. No. 16/382,885, Response to Jun. 5, 2020 Final office action filed Jul. 31, 2020, 9 pages.
Co-Pending U.S. Appl. No. 16/382,885, Response to Nov. 29, 2019 Non-Final office action filed Mar. 2, 2020.
Co-Pending U.S. Appl. No. 16/382,885, Response to restriction requirement dated Oct. 2, 2019, 3pgs.
Co-Pending U.S. Appl. No. 16/382,885, Restriction Requirement dated Aug. 9, 2019, 7 pgs.
Co-Pending U.S. Appl. No. 16/398,845, Interview Summary dated Dec. 18, 2019, 7 pages.
Co-Pending U.S. Appl. No. 16/398,845, Non-Final Office Action dated Aug. 6, 2019, 25 pages.
Co-Pending U.S. Appl. No. 16/398,845, Notice of Allowance dated Jan. 21, 2020, 11 pages.
Co-Pending U.S. Appl. No. 16/398,845, Response to Non-Final Office Action dated Nov. 6, 2019, 9 pages.
Co-Pending U.S. Appl. No. 16/418,614, Interview Summary dated Dec. 18, 2019, 7 pages.
Co-Pending U.S. Appl. No. 16/418,614, Non-Final Office Action dated Aug. 6, 2019, 31 pages.
Co-Pending U.S. Appl. No. 16/418,614, Notice of Allowance dated Jan. 30, 2020, 12 pages.
Co-Pending U.S. Appl. No. 16/418,614, Response to Non-Final Office Action dated Nov. 6, 2019, 10 pages.
Co-Pending U.S. Appl. No. 16/424,788 Corrected Notice of Allowance, dated Jan. 7, 2021, 5 pages.
Co-Pending U.S. Appl. No. 16/424,788 Non-Final Office Action, dated Nov. 29, 2019, 24 pgs.
Co-Pending U.S. Appl. No. 16/424,788 Non-Final Office Action, dated Nov. 5, 2020, 8 pgs.
Co-Pending U.S. Appl. No. 16/424,788 Notice of Allowance, dated Dec. 17, 2020, 9 pages.
Co-Pending U.S. Appl. No. 16/424,788 Response to Nov. 29, 2019 Non-Final Office Action, filed Mar. 2, 2020.
Horak, Friedrich, "Effectiveness of twice daily azelastine nasal spray in patients with seasonal allergic rhinitis," Ther. Clin. Risk Manag., Oct. 2008; 4(5): 1009-1022.
Hou, Ruihua and Baldwin, David S., "A neuroimmunological perspective on anxiety disorders", Human Psychopharmacol Clin Exp. 2012, vol. 27: 6-14.
Hou, Ruihua et al., "Peripheral inflammatory cytokines and immune balance in Generalized Anxiety Disorder: case-controlled study", Brain Behav Immun. May 2017; 62: 212-218.
Jeon, Sang Won and Kim, Yong Ku, "Detrimental effect of preservative in eye drops: Neuroinflammation and cytokine abnormality in major depression: Cause or consequence in that illness?" World Journal of Psychiatry, Sep. 22, 2016; 6(3): 283-293.

(56) References Cited

OTHER PUBLICATIONS

Jones, Patrice et al. "Folate and Inflammation—links between folate and features of inflammatory conditions", Journal of Nutrition & Intermediary Metabolism 18 (2019) 100104, 6 pages.

Kappelmann, N. et al., "Antidepressant activity of anti-cytokine treatment: a systematic review and meta-analysis of clinical trials of chronic inflammatory conditions", Molecular Psychiatry, 2018, vol. 23, 335-313.

Kempuraj, Duraisamy, et al. 2003, Azelastine Inhibits Secretion of IL-6, TNF-alpha and IL-8 as Well as NF-kappaB Activation and Intracellular Calcium Ion Levels in Normal Human Mast Cells. Int Arch Allergy Immunol. 132 (3), 231-9 Nov. 2003.

Kohler, Ole et al., "Inflammation in Depression and the Potential for Anti-Inflammatory Treatment." Current Neuropharmacology, 2016, 11, 732-712.

Kolb, Andreas F. and Petrie, Linda, "Folate deficiency enhances the inflammatory response of macrophages", Mol Immunol. Jun. 2013; 54(2):164-172.

Koo, Ja Wook et al., 2010, Nuclear factor-κB is a critical mediator of stress impaired neurogenesis and depressive behavior. PNAS, Feb. 9, 2010, vol. 107 (6) 2669-2674.

Leon, Michael, Sawmiller, Darrell, Shytle, R. Douglas, and Tan, Jun. 2018. Therapeutic Cocktail Approach for Treatment of Hyperhomocysteinemia in Alzheimer's Disease Cell Med. 2018; 10:2155179017722280.

Liu, Chun-Hong et al., Role of inflammation in depression relapse, Journal of Neuroinflammation (2019) 16:90, 11 pages.

Maeng, Sung Ho and Hong, Heeok, "Inflammation as the Potential Basis in Depression." Int Neurourol J 2019; vol. 23(Suppl 2): S63-71.

Naddafi, F., Mirshafiey A., The neglected role of histamine in Alzheimer's disease., Jun. 2013;28(4):327-36. doi: 10.1177/1533317513488925. Epub May 15, 2013.

Niazi, Sarfaraz K., Handbook of Pharmaceutical Manufacturing Formulations vols. 1-6, 2004, 304 pages.

Niraula, Anzela et al., "IL-6 Induced by Social Stress Promotes a Unique Transcriptional Signature in the Monocytes That Facilitate Anxiety." Biol Psychiatry 85 (8), 679-689, Apr. 15, 2019.

Reynolds, Edward, "Vitamin B12, folic acid, and the nervous system", The Lancet Neurology, Nov. 2006, Abstract, 35 pages.

Riethmuller et al. Arzneimittel-Forschung, 1994, vol. 44, No. 10, pp. 1136-1140.

Sedeyn, Jonathan Histamine Induces Alzheimer's Disease-Like Blood Brain Barrier Breach and local cellular Responses in Mouse Brain Organotypic Culture. Hindawi Aug. 21, 2015.

Simons, F.E., Simons, K.J. Clinical pharmacology of new histamine H1 receptor antagonist. Clin Pharmacokinet. 1999;36:329-352.

Starkstein, et al.,"The construct of generalized anxiety disorder in altheimer's disease," Am J Geriatr Psychiatry Jan. 2007. 15(1) 42-49.

St-Jean, Genevieve; Turcotte, Isabelle; Bastien, Celyne H. Cerebral asymmetry in insomnia sufferers. Frontiers in Neurology 2012, 3, 1-12.

Szelenyi, I., Achterrath-Tuckermann, U., Schmidt, J., Minker, E., Paegelow, I., Werner, H. Azelastine: A multifaceted drug for asthma therapy. Agents Actions Suppl. 1991;34:295-311 (abstract).

Tanaka, Hibiki, Hashimoto, Mamoru, et al, 2015. Relationship Between Dementia Severity and Behavioural and Psychological Symptoms in Early-Onset Alzheimer's Disease. Psychogeriatrics. Dec. 2015;15(4):242-7.

Troubat, Romain et al., Neuroinflammation and Depression: A Review. Eur J Neurosci. Mar. 9, 2020 DOI: 10.1111/ejn.14720.

Williams, Patricia B, Crandall, Elizabeth, and Sheppard, John D, 2010, Azelastine hydrochloride, a dual-acting anti-inflammatory ophthalmic solution, for treatment of allergic conjunctivitis. Clinical Ophthalmology 2010:4 993-1001.

Yoneda, Kazunori, et al. 1997, Suppression by Azelastine Hydrochloride of NF-KB Activation Involved in Generation of Cytokines and Nitric Oxide. Japanese Journal of Pharmacology, 73:145-53.

Zacny, James P., Paice, Judith A., and Coalson, Dennis W., 2012. Separate and combined psychopharmacological effects of alprazolam and oxycodone in healthy volunteers, Aug. 1, 2012; 124(3): 274 282.

(Wang, Jianmin) Co-Pending U.S. Appl. No. 17/546,342, filed Dec. 9, 2021, Specification and Claims.

(Wang, Jianmin) Co-Pending U.S. Appl. No. 17/673,136, filed Feb. 16, 2022, Specification and Claims.

(Wang, Jianmin) Co-Pending Application No. PCT/US22/16545, filed Feb. 16, 2022, Specification and Claims.

(Wang, Jianmin) Co-Pending Australia National Stage Application No. 2019443520, Effective Filing Date Apr. 30, 2019, Specification and Claims (See PCT/US19/29885, which published as WO 2020/222799, for Specification and Claims as filed).

(Wang, Jianmin) Co-Pending Australia National Stage Application No. 2019445048, Effective Filing Date Apr. 12, 2019, Specification and Claims (See PCT/US19/27293, which published as WO 2020/209872, for Specification and Claims as filed).

(Wang, Jianmin) Co-Pending Australia National Stage Application No. 2019446955, Effective Filing Date May 21, 2019, Specification and Claims (See PCT/US19/33359, which published as WO2020/236159, for Specification and Claims as filed).

(Wang, Jianmin) Co-Pending Canada National Stage Application No. 3,136,633, filed Oct. 8, 2021, Specification and Claims, 25 pages.

(Wang, Jianmin) Co-Pending Canada National Stage Application No. 3,137,393, Filed Oct. 19, 2021, Specification and Claims, 17 pages.

(Wang, Jianmin) Co-Pending Canada National Stage Application No. 3,139,082, Filed Nov. 3, 2021, Claims and Amended Specification, 25 pages.

(Wang, Jianmin) Co-Pending China National Stage Application No. 201980095322.X, filed Oct. 11, 2021, Specification and Claims (32 pages) (see PCT/US19/27293, which published as WO2020/209872 for English Translation).

(Wang, Jianmin) Co-Pending China National Stage Application No. 201980095741.3, Filed Oct. 25, 2021, Specification and Amended Claims as filed (26 pages) with English Translation of the Amended Claims (2 pages) (See PCT/US19/29885, which published as WO 2020/222799, for English Translation of the Specification).

(Wang, Jianmin) Co-Pending China National Stage Application No. 201980096574.4, Filed Nov. 18, 2021, Specification and Amended Claims as filed (48 pages) with English Translation of the Amended Claims (4 pages) (See PCT/US19/33359, which published as WO2020/236159, for English Translation of the Specification).

(Wang, Jianmin) Co-Pending European National Stage Application No. 19924315.5, filed Nov. 11, 2021, Specification and Amended Claims as filed (34 pages).

(Wang, Jianmin) Co-Pending European National Stage Application No. 19927207.1, filed Nov. 29, 2021, Specification and Amended Claims as filed (26 pages).

(Wang, Jianmin) Co-Pending European National Stage Application No. 19929933.0, filed Dec. 21, 2021, Specification and Amended Claims as filed (35 pages).

(Wang, Jianmin) Co-Pending Japan National Stage Application No. 2021-556914, filed Sep. 17, 2021, Specification and Claims (19 pages) (see PCT/US19/27293, which published as WO2020/209872, for English Translation).

(Wang, Jianmin) Co-Pending Japan National Stage Application No. 2021-558496, filed Sep. 21, 2021, Specification and Claims (15 pages) (See PCT/US19/29885, which published as WO2020/222799, for English Translation).

(Wang, Jianmin) Co-Pending Japan National Stage Application No. 2021-566489, filed Nov. 9, 2021, Request for Entry and Specification and Claims (18 pages) (See PCT/US19/33359, which published as WO2020/236159, for English Translation of Specification and Claims).

Co-Pending U.S. Appl. No. 16/831,330, Notice of Allowance dated Aug. 3, 2021, 8 pages.

Co-Pending U.S. Appl. No. 16/834,146, Non-Final Office Action dated Nov. 15, 2021, 29 pages.

Co-Pending U.S. Appl. No. 16/834,146, Response to Nov. 15, 2021 Non-Final Office Action, dated Feb. 22, 2022, 9 pages.

(56) References Cited

OTHER PUBLICATIONS

Co-Pending U.S. Appl. No. 16/884,459, Final Office Action dated Dec. 10, 2021, 19 pages.
Co-Pending U.S. Appl. No. 16/884,459, Response to Sep. 14, 2021 Non-Final Office Action, filed Nov. 16, 2021, 9 pages.
Co-Pending U.S. Appl. No. 16/913,927, Final Office Action dated Dec. 3, 2021, 12 pages.
Co-Pending U.S. Appl. No. 16/913,927, Response to Aug. 11, 2021 Non-Final Office Action, dated Nov. 10, 2021, 6 pages.
Co-Pending U.S. Appl. No. 17/094,405, Response to Jul. 30, 2021 Final Office Action, dated Sep. 30, 2021, 10 pages.
Co-Pending U.S. Appl. No. 17/459,868, Preliminary Amendment, filed Aug. 27, 2021, 8 pages.
Co-Pending Application No. PCT/US21/44654, International Search Report and Written Opinion, dated Nov. 15, 2021, 10 pages.
Co-Pending China National Stage Application No. 201980095322.X, English Version of Amended Claims as filed Oct. 11, 2021, 3 pages.
Hua, S. "Advances in Nanoparticulate Drug Delivery Approaches for Sublingual and Buccal Administration". Nov. 10, 2019 (Article 1328), pp. 1-9.
Munoz-Cano et al. "Severity of Allergic Rhinitis Impacts Sleep and Anxiety: Results from a Large Spanish Cohort". Clinical and Translational Allergy, 2018, 8 (Article 23), p. 1-9.
Co-Pending U.S. Appl. No. 16/424,788 Response to Nov. 5, 2020 Non-Final Office Action, dated Dec. 2, 2020, 6 pages.
Co-Pending U.S. Appl. No. 16/424,788 Response to Restriction Requirement, dated Oct. 2, 2019, 3 pgs.
Co-Pending U.S. Appl. No. 16/424,788 Restriction Requirement, dated Aug. 9, 2019, 7 pgs.
Co-Pending U.S. Appl. No. 16/424,788, Final Office Action dated Aug. 28, 2020, 17 pages.
Co-Pending U.S. Appl. No. 16/424,788, Response to Aug. 28, 2020 Final Office Action filed Oct. 19, 2020, 6 pages.
Co-Pending U.S. Appl. No. 16/426,121, Interview Summary dated Dec. 18, 2019, 7 pages.
Co-Pending U.S. Appl. No. 16/426,121, Non-Final Office Action dated Aug. 6, 2019, 25 pages.
Co-Pending U.S. Appl. No. 16/426,121, Notice of allowance dated Jan. 21, 2020, 18 pages.
Co-Pending U.S. Appl. No. 16/426,121, Response to Non-Final Office Action dated Nov. 6, 2019, 9 pages.
Co-Pending U.S. Appl. No. 16/831,330, Non-Final Office Action dated Apr. 7, 2021, 16 pages.
Co-Pending U.S. Appl. No. 16/831,330, Response to Apr. 7, 2021 Non-Final Office Action filed Jul. 21, 2021, 7 pages.
Co-Pending U.S. Appl. No. 16/884,459, filed Dec. 15, 2020 Final Office Action, 15 pages.
Co-Pending U.S. Appl. No. 16/884,459, Non-Final Office Action dated Aug. 11, 2020, 35 pages.
Co-Pending U.S. Appl. No. 16/884,459, Non-Final Office Action dated Sep. 14, 2021, 35 pages.
Co-Pending U.S. Appl. No. 16/884,459, Response to Aug. 11, 2020 Non-Final Office Action dated Nov. 12, 2020, 11 pages.
Co-Pending U.S. Appl. No. 16/884,459, Response to Dec. 15, 2020 Final Office Action, filed Mar. 15, 2021, 30 pages.
Co-Pending U.S. Appl. No. 16/884,553, Non-Final Office Action dated Aug. 11, 2020, 26 pages.
Co-Pending U.S. Appl. No. 16/884,553, Notice of Allowance dated Dec. 2, 2020, 9 pages.
Co-Pending U.S. Appl. No. 16/884,553, Response to Aug. 11, 2020 Non-Final Office Action dated Nov. 12, 2020, 8 pages.
Co-Pending U.S. Appl. No. 16/913,927, Final Office Action dated Jun. 2, 2021, 16 pages.
Co-Pending U.S. Appl. No. 16/913,927, Non-Final Office Action dated Aug. 11, 2021, 17 pages.
Co-Pending U.S. Appl. No. 16/913,927, Non-Final Office Action dated Feb. 19, 2021, 19 pages.
Co-Pending U.S. Appl. No. 16/913,927, Non-Final Office Action dated Nov. 9, 2020, 24 pages.
Co-Pending U.S. Appl. No. 16/913,927, Response to Aug. 27, 2020 Restriction Requirement, filed Oct. 20, 2020, 5 pages.
Co-Pending U.S. Appl. No. 16/913,927, Response to Feb. 19, 2021 Non-Final Office Action filed May 19, 2021, 10 pages.
Co-Pending U.S. Appl. No. 16/913,927, Response to Jun. 2, 2021 Final Office Action, dated Jul. 30, 2021, 6 pages.
Co-Pending U.S. Appl. No. 16/913,927, Response to Nov. 9, 2020 Non-Final Office Action filed Feb. 5, 2021, 8 pages.
Co-Pending U.S. Appl. No. 16/913,927, Restriction Requirement dated Aug. 27, 2020, 5 pages.
Co-Pending U.S. Appl. No. 17/094,405, Final Office Action dated Jul. 30, 2021, 22 pages.
Co-Pending U.S. Appl. No. 17/094,405, Non-Final Office Action dated Apr. 14, 2021, 21 pages.
Co-Pending U.S. Appl. No. 17/094,405, Response to Apr. 14, 2021 Non-Final Office Action filed Jul. 14, 2021, 7 pages.
Co-Pending U.S. Appl. No. 17/094,405, Response to Jan. 26, 2021 Restriction Requirement, filed Apr. 5, 2021, 7 pages.
Co-Pending U.S. Appl. No. 17/094,405, Restriction Requirement dated Jan. 26, 2021, 5 pages.
Co-Pending application No. PCT/US19/29885 International Search Report and Written Opinion dated Jul. 15, 2019. 7 pages.
Co-Pending application No. PCT/US19/33359 International Search Report and Written Opinion dated Aug. 15, 2019. 9 pages.
Co-Pending Application No. PCT/US20/34735, International Search Report and Written Opinion dated Aug. 17, 2020, 10 pages.
Co-Pending Application No. PCT/US20/39916, International Search Report and Written Opinion dated Oct. 8, 2020, 8 pages.
Co-Pending Application No. PCT/US20/59846, International Search Report and Written Opinion dated Mar. 8, 2021, 8 pages.
Co-Pending Application No. PCT/US2019/027293, Corrected Written Opinion, dated Oct. 29, 2019, 5 pages.
Co-Pending Application No. PCT/US2019/027293, Search Report & Written Opinion, dated Sep. 17, 2019, 8 pages.
Cummings et al. "Effect of Dextromethorphan-Quinidine on Agitation in Patients with Alzheimer Disease Dimentia: A Randomized Clinical Trial". JAMA, 2015; 314(12):1242-1254.
Feng, Dan et al. "Folic acid inhibits lipopolysaccharide-induced inflammatory response in RAW264.7 macrophages by suppressing MAPKs and NF-kB activation", Inflamm Res. Sep. 2011;60(9):817-822.
Galatowicz, G, Ajayi Y, Stern ME, Calder VL. Ocular antiallergic compounds selectively inhibit human mast cell cytokines in vitro and conjunctival cell infiltration in vivo. Clin Exp Allergy. 2007; 37:1648-1656.
Georgin-Lavialle, S. et al., "Mast Cells' Involvement in Inflammation Pathways Linked to Depression: Evidence in Mastocytosis." Mol Psychiatry. 21 (11), 1511-1516 Nov. 2016.
Goedert, M., Spillantini, M.G,. 2006. A century of Alzheimer's disease. Science, 314:777-81.
Guignet, Michelle et al., "Persistent behavior deficits, neuroinflammation, and oxidative stress in a rat model of acute organophosphate intoxication", vol. 133, Jan. 2020, 101131.
Hansen et al. Clinical Interventions in Aging 2008, vol. 3, No. 2, pp. 211-225.
Hashiro et al. "A Combination Therapy of Psychotropic Drugs and Antihistaminics or Antiallergics in Patients with Chronic Urticaria". Journal of Dermatological Sciences, 1996; 11:209-213.
Hatakeyama, Aiko, Masahiko Fujii, Reiko Hatakeyama, Yumiko Fukuoka, Takuma Satoh-Nakagawa and Hidetada Sasaki, Azelastine hydrochloride on behavioral and psychological symptoms and activities of daily living in dementia patients, Geriatr Gerontol Int 2008; 8: 59-61 (2008).
Hazama, H., Nakajima, T., Hisada, T., Hamada, E., Omata, M., Kurachi, Y. Effects of azelastine on membrane currents in tracheal smooth muscle cells isolated from the guinea-pig. Eur J Pharmacol. 1994;259: 143-150.
Co-Pending U.S. Appl. No. 16/884,459, Response to Dec. 10, 2021 Final Office Action, filed Feb. 25, 2022, 18 pages.
Co-Pending U.S. Appl. No. 16/884,459, Rule 132 Declaration dated Feb. 24, 2022, 4 pages.
Co-Pending U.S. Appl. No. 16/913,927, Response to Dec. 3, 2021 Final Office Action, dated Mar. 3, 2022, 3 pages.

(56) References Cited

OTHER PUBLICATIONS

Bartlett, D. and Bear, M., "Rhinorrhea as a Result of Alzheimer's Disease Treatment: A Case Report", The Senior Dare Pharmacist. Dec. 2019; 34(10):669-673, 5 pages.
Co-Pending U.S. Appl. No. 16/834,146, Final Office Action dated Mar. 18, 2022, 20 pages.
Co-Pending U.S. Appl. No. 16/913,927, Notice of Allowance dated Mar. 21, 2022, 11 pages.

\* cited by examiner

PHARMACEUTICAL COMPOSITIONS AND METHODS FOR TREATMENT OF PSYCHIATRIC DISORDERS

FIELD OF THE INVENTION

The invention relates to the field of practical medicine, namely, to the use of pharmaceutical compositions for treating, preventing and/or alleviating manifestations of one or more psychiatric disorders or symptoms thereof, including anxiety or depression disorders, such as major depressive disorder, generalized anxiety disorder, panic disorder, agitation, social anxiety disorder, mild chronic depression, obsessive-compulsive disorder, premenstrual dysphoric disorder, seasonal affective disorder, childhood enuresis, dysthymia, bipolar disorder, posttraumatic stress disorder and sleep disorder related to anxiety.

BACKGROUND OF THE INVENTION

Anxiety, depression, panic disorder, and agitation, affect more than one in ten people globally (10.7%) as reported by the Institute for Health Metrics and Evaluation in their flagship Global Burden of Disease study in 2017. Two examples of psychiatric disorders, major depressive disorders (MDDs) and generalized anxiety disorder (GAD), are common, severe, chronic and often life-threatening illnesses. More than 20% of the adult population suffers from these conditions at some time during their life. Suicide is estimated to be a cause of death in up to approximately 15% of individuals with MDDs. In addition, MDDs represent a major risk factor for the development of cardiovascular disease and death after myocardial infarction.

Treatments for anxiety, depression and the like include selective serotonin reuptake inhibitors (SSRIs), such as citalopram (Celexa), escitalopram oxalate (Lexapro), fluoxetine (Prozac), fluvoxamine (Luvox), paroxetine HRI (Paxil), and sertraline (Zoloft); selective serotonin & norepinephrine inhibitors (SNRIs), such as desvenlafaxine (Khedezla), desvenlafaxine succinate (Pristiq), duloxetine (Cymbalta), levomilnacipran (Fetzima), and venlafaxine (Effexor); tetracyclic antidepressants of noradrenergic and specific serotonergic antidepressants (NaSSAs), such as Remeron; tricyclic antidepressants, such as Elavil, imipramine (Tofranil), nortriptyline (Pamelor), and Sinequan; monoamine oxidase inhibitors (MAOIs), such as isocarboxazid (Marplan), phenelzine (Nardil), selegiline (EMSAM), and tranylcypromine (Parnate); and benzodiazepines, such as alprazolam (Xanax), diazepam (Valium), buspirone (Buspar), and lorazepam (Ativan). These drugs do carry a risk of addiction, tolerance, loss of effectiveness, inciting violent or self-destructive actions, fatigue, and drowsiness along with nausea, increased appetite and weight gain, loss of sexual desire and other sexual problems, insomnia, dry mouth, blurred vision, and so on.

Clinically, new treatments are highly and urgently needed that have tremendous improvement and significant impact to the management of patients with psychiatric disorders, such as treatments being highly effective and with much less adverse effects.

Treatments of psychiatric disorders based on pharmacological mechanisms of action of SSRI, SNRI, NaSSA and MAOI have shown their limitations. Increasing evidence indicates that inflammatory processes can cause and contribute to the development of psychiatric disorders.

Inflammation can be defined as one of the immune responses for protecting living organisms from damage. The immune system can be triggered by various factors such as pathogens, damage to cells and stress that may induce acute or chronic inflammatory responses in organs including the brain, potentially leading to tissue damage or disease. The latest advancements in neurobiological research provide increasing evidence that inflammatory and neurodegenerative pathways play a relevant role in depression and anxiety. Preclinical and clinical studies on depression and anxiety highlighted an increased production of inflammatory markers, such as interleukin (IL)-1, IL-6, tumor necrosis factor (TNF)-$\alpha$ and interferon (INF)-$\alpha$ and $\gamma$, and overactivated inflammatory signaling pathways including nuclear factor kappa B (NF-$\kappa$B). Other studies show that acute and chronic administration of cytokines or cytokine inducers were found to trigger depressive and/or anxiety symptoms. According to the cytokine hypothesis, depression and anxiety would be due to a stress-related increased production of pro-inflammatory cytokines that, in turn, would lead to increased oxidative and nitrosative brain damage and consequent reduced availability of tryptophan and serotonin (5-HT). Cytokines would also play a role in the onset of the glucocorticoid resistance, underlying the overdrive of the hypothalamic-pituitary-adrenal axis. Therefore, activation of the inflammatory and neurodegenerative pathways would lead to the brain damage observed in depression and/or anxiety through both reduced neurogenesis and increased neurodegeneration.

Azelastine is classified pharmacologically as a second-generation antihistamine and is a relatively selective, non-sedative, competitive antagonist at $H_1$ receptors for treatment of allergic rhinitis and asthma. But, more uniquely, its inhibition of inflammatory mediators and its mast cell stabilizing effects, in addition to its antihistaminic activity, place it among the new generation of dual-acting anti-inflammatory drugs. Its ability to modify several other mediators of inflammation, such as IL-1, IL-6, TNF-$\alpha$ and INF-$\alpha$, and to reduce overactivation of NF-$\kappa$B inflammatory signaling pathway might contribute to its mechanism of action of potential treatment of psychiatric disorders, such as anxiety, depression, panic disorder, agitation, bipolar disorder (BD), and premenstrual dysphoric disorder (PDD). In vitro and in vivo studies, as well as clinical trials, support the dual effects of direct inhibition and stabilization of inflammatory cells. In vitro data indicate that azelastine's affinity for inhibition of mast cell degranulation may also decrease the release of other inflammatory mediators, including leukotrienes and interleukin-1$\beta$, among others. Preclinical studies show that azelastine also directly antagonizes other mediators of inflammation, such as tumor necrosis factor-$\alpha$, leukotrienes, endothelin-1, and platelet-activating factor.

Folic acid, a form of vitamin B9, is important for the synthesis and repair of DNA and other genetic material, and it is necessary for cells to divide and for functioning of the nervous system at all ages. It facilitates the methionine-synthase mediated conversion of homocysteine to methionine and that is important for nucleotide synthesis and genomic and non-genomic methylation. It has been known that the methylation processes are central to the biochemical basis of the neuropsychiatry of folic acid deficiency. There is also considerable evidence that impaired methylation has some etiologic significance in depression, dementia and folic acid deficiency may specifically affect central monoamine neurotransmitter metabolism and lead to an increase in depressive disorders.

The deficiency of folate, the nature form of folic acid, is shown to reduce proliferation in multiple cell types by causing nucleotide imbalances and subsequent accumulation of cells in the S phase and changes in folate levels may also manipulate the proliferation of T cells which is often associated with various chronic inflammatory disorders. Studies have demonstrated that folic acid significantly attenuated the release of proinflammatory mediators in LPS-activated microglia, blocking NF-κB, and overregulating IL-10 dependent suppressors of cytokine signaling proteins expression through p38 pathways, and effects production of inflammatory markers, such as interleukin (IL)-1, IL-6, tumor necrosis factor (TNF)-α.

Therefore, a unique combination of azelastine (antihistamine agent with anti-inflammatory activities) with folic acid or folate, and/or salts, metabolites, or derivatives thereof would potentially be, in terms of working through multi-mechanisms of actions, an effective treatment for behavioral and psychiatric disorders.

SUMMARY OF THE INVENTION

The present invention includes a pharmaceutical composition that comprises two active pharmaceutical ingredients. This pharmaceutical composition comprises the first active ingredient that is azelastine or a pharmaceutically acceptable salt of azelastine and the second active ingredient that is folic acid or folate, and/or salts, metabolites, or derivatives thereof.

In some embodiments of this invention, the pharmaceutically acceptable salt of azelastine in the pharmaceutical composition is azelastine hydrochloride.

In some embodiments of this invention, azelastine hydrochloride (and/or other salt thereof) in the pharmaceutical composition is provided in an amount of about 1 mg to about 8 mg and folic acid or folate, and/or salts, metabolites, or derivatives thereof in an amount of about 0.1 mg to about 2 mg.

The present invention also includes an oral pharmaceutical dosage form of the pharmaceutical composition that is a solid, liquid, gel, or solution form.

The present invention further includes use of the composition, such as by oral dosage, through administration to patients with psychiatric disorders, such as one or more of major depressive disorder (MDD), generalized anxiety disorder (GAD), panic disorder, agitation, social anxiety disorder (SAD), mild chronic depression (MCD), obsessive-compulsive disorder (OCD), premenstrual dysphoric disorder (PDD), seasonal affective disorder (SAD), dysthymia, bipolar disorder, posttraumatic stress disorder (PSD) and sleep disorders related to anxiety (SDRA).

In some embodiments of this invention, an oral pharmaceutical dosage form of the pharmaceutical composition containing azelastine hydrochloride (and/or other salt thereof) in an amount of about 1 mg to about 8 mg and folic acid or folate, and/or salts, metabolites, or derivatives thereof in an amount of about 0.1 mg to about 2 mg is administered to patients with any one or more psychiatric disorder, such as one or more of major depressive disorder (MDD), generalized anxiety disorder (GAD), panic disorder, agitation, social anxiety disorder (SAD), mild chronic depression (MCD), obsessive-compulsive disorder (OCD), premenstrual dysphoric disorder (PDD), seasonal affective disorder (SAD), dysthymia, childhood enuresis, bipolar disorder, posttraumatic stress disorder (PSD or PTSD) and sleep disorders related to anxiety (SDRA).

Embodiments include Aspect 1, which are pharmaceutical compositions comprising: azelastine or a pharmaceutically acceptable salt of azelastine; folic acid or folate, and/or salts, metabolites, or derivatives thereof; and one or more pharmaceutically acceptable excipients.

Aspect 2 is the pharmaceutical composition of Aspect 1, wherein the azelastine or the pharmaceutically acceptable salt of azelastine is present in the pharmaceutical composition in an amount in the range of about 1 mg to about 8 mg, or present at least in some amount and up to about 8 mg, such as in the range of about 2-8 mg, or about 3-7 mg, or about 4-6 mg, or any range in between.

Aspect 3 is the pharmaceutical composition of Aspect 1 or 2, wherein the folic acid or folate, and/or salt, metabolite, or derivative thereof is present in the pharmaceutical composition in an amount in the range of about 0.1 mg to about 2 mg, or present at least in some amount and up to about 2 mg, such as in the range of about 0.2 mg to about 0.9 mg, or about 0.3 mg to about 0.8 mg, or about 0.4 mg to about 0.7 mg, or about 0.5 mg to about 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, or 1.9 mg, or any range in between.

Aspect 4 is the pharmaceutical composition of any of Aspects 1-3, wherein the folic acid or folate, and/or salt, metabolite, or derivative thereof is present in the pharmaceutical composition in an amount in the range of about 0.1 mg to about 0.4 mg.

Aspect 5 is the pharmaceutical composition of any of Aspects 1-4, wherein: the azelastine or the pharmaceutically acceptable salt of azelastine is present in the pharmaceutical composition in an amount in the range of about 1 mg to about 6 mg, such as in the range of about 1-4 mg and the folic acid or folate, and/or salt, metabolite, or derivative thereof is present in the pharmaceutical composition in an amount in the range of about 0.1 mg to about 2 mg, such as in the range of about 0.1-0.4 mg; or the azelastine or the pharmaceutically acceptable salt of azelastine is present in the pharmaceutical composition in an amount in the range of about 1 mg to about 8 mg, and the folic acid is present in the pharmaceutical composition in an amount in the range of about 0.1-1.0 mg or about 0.1-0.4 mg.

Aspect 6 is the pharmaceutical composition of any of Aspects 1-5, wherein the pharmaceutically acceptable salt of azelastine is azelastine hydrochloride.

Aspect 7 is the pharmaceutical composition of any of Aspects 1-6, wherein the pharmaceutically acceptable salt of azelastine is azelastine hydrochloride and is present in an amount in the range of up to about 8 mg.

Aspect 8 is the pharmaceutical composition of any of Aspects 1-7, wherein the azelastine hydrochloride is present in an amount in the range of about 1 mg to about 4 mg.

Aspect 9 is the pharmaceutical composition of any of Aspects 1-8, wherein the pharmaceutical composition is formulated as an oral pharmaceutical dosage form.

Aspect 10 is the pharmaceutical composition of any of Aspects 1-9, wherein the oral pharmaceutical dosage form is a solid form or a liquid form.

Aspect 11 is a method comprising: administering a pharmaceutical composition to a patient; wherein the pharmaceutical composition comprises effective amounts of azelastine or a pharmaceutically acceptable salt of azelastine and folic acid or folate, and/or salts, metabolites, or derivatives thereof; and wherein the effective amounts together are sufficient to treat one or more symptoms of one or more psychiatric disorder of the patient.

Aspect 12 is the method of Aspect 11, wherein one or more of the psychiatric disorders or symptoms of psychiatric disorders are selected from major depressive disorders, generalized anxiety disorder, panic disorder, agitation, social anxiety disorder, mild chronic depression, premenstrual dysphoric disorder, obsessive-compulsive disorder, dysthymia, childhood enuresis, bipolar disorder, posttraumatic stress disorder, seasonal affective disorder, and anxiety-related sleep disorder.

Aspect 13 is the method of Aspect 11 or 12, wherein the pharmaceutical composition is administered once or twice a day, or once every 2 or 3 or 4 days to the patient, such as in an oral solid or liquid form.

Aspect 14 is the method of any of Aspects 11-13, wherein the azelastine or the pharmaceutically acceptable salt of azelastine is present in the pharmaceutical composition in an amount in the range of about 1 mg to about 8 mg, or present at least in some amount and up to about 8 mg, such as in the range of about 2-8 mg, or about 3-7 mg, or about 4-6 mg, or any range in between.

Aspect 15 is the method of any of Aspects 11-14, wherein the folic acid or folate, and/or salt, metabolite, or derivative thereof is present in the pharmaceutical composition in an amount in the range of about 0.1 mg to about 2 mg, or present at least in some amount and up to about 2 mg, such as in the range of about 0.2 mg to about 0.9 mg, or about 0.3 mg to about 0.8 mg, or about 0.4 mg to about 0.7 mg, or about 0.5 mg to about 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, or 1.9 mg, or any range in between.

Aspect 16 is the method of any of Aspects 11-15, wherein the folic acid or folate, and/or salt, metabolite, or derivative thereof is present in the pharmaceutical composition in an amount in the range of about 0.1 mg to about 0.4 mg.

Aspect 17 is the method of any of Aspects 11-16, wherein the azelastine or the pharmaceutically acceptable salt of azelastine is present in the pharmaceutical composition in an amount in the range of about 1 mg to about 4 mg.

Aspect 18 is the method of any of Aspects 11-17, wherein: the azelastine or the pharmaceutically acceptable salt of azelastine is present in the pharmaceutical composition in an amount in the range of about 1 mg to about 8 mg; and the folic acid or folate, and/or salt, metabolite, or derivative thereof is present in the pharmaceutical composition in an amount in the range of about 0.1 mg to about 2 mg, such as from about 0.1 mg to about 1 mg.

Aspect 19 is a pharmaceutical composition comprising at least some amount of azelastine, or a pharmaceutically acceptable salt of azelastine, in an amount up to about 8 mg (such as in the range of about 2-8 mg, or about 3-7 mg, or about 4-6 mg, or any range in between), and comprising folic acid, and one or more pharmaceutically acceptable excipients.

Aspect 20 is the pharmaceutical composition of Aspect 19, wherein the folic acid or folate, and/or salt, metabolite, or derivative thereof is present in the pharmaceutical composition at least in some amount and in the range of up to about 2 mg, such as in the range of about 0.2 mg to about 0.9 mg, or about 0.3 mg to about 0.8 mg, or about 0.4 mg to about 0.7 mg, or about 0.5 mg to about 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, or 1.9 mg, or any range in between.

Aspect 21 is the pharmaceutical composition of Aspect 19 or 20, wherein the azelastine or the pharmaceutically acceptable salt of azelastine is present in the pharmaceutical composition in an amount that is 1, 2, 3, 4 or 5 times the amount of the folic acid present in the pharmaceutical composition.

Aspect 22 is the pharmaceutical composition of any of Aspects 19-21, wherein the azelastine or the pharmaceutically acceptable salt of azelastine is present in the pharmaceutical composition in an amount in the range of about 2 mg, and the folic acid or folate, and/or salt, metabolite, or derivative thereof is present in the pharmaceutical composition at least in some amount, which is an amount of up to about 0.5 mg.

Aspect 23 is the pharmaceutical composition of any of Aspects 19-22, wherein the pharmaceutically acceptable salt of azelastine is azelastine hydrochloride.

Aspect 24 is the pharmaceutical composition of any of Aspects 19-23, wherein the pharmaceutical composition is formulated as an oral pharmaceutical dosage form.

Aspect 25 is a method comprising administering a pharmaceutical composition to a patient, wherein the pharmaceutical composition comprises azelastine, or a pharmaceutically acceptable salt of azelastine, and folic acid or folate, and/or salt, metabolite, or derivative thereof.

Aspect 26 is the method of Aspect 25, wherein the pharmaceutical composition is administered once or twice a day, or once every 2 or 3 or 4 days to the patient, optionally in an oral solid or liquid form.

Aspect 27 is the method of Aspect 25 or 26, wherein the pharmaceutical composition is administered for a period of at least 2 weeks.

Aspect 28 is the method of any of Aspects 25-27, wherein the azelastine or the pharmaceutically acceptable salt of azelastine is present in the pharmaceutical composition in an amount in the range of about 1 mg to about 8 mg.

Aspect 29 is the method of any of Aspects 25-28, wherein the azelastine or the pharmaceutically acceptable salt of azelastine is present in the pharmaceutical composition in an amount that is 1, 2, 3, 4 or 5 times the amount of folic acid or folate, and/or salt, metabolite, or derivative thereof present in the pharmaceutical composition.

Aspect 30 is the method of any of Aspects 25-29, wherein the folic acid or folate, and/or salt, metabolite, or derivative thereof is present in the pharmaceutical composition in an amount in the range of about 0.1 mg to about 2 mg.

Aspect 31 is the method of any of Aspects 25-30, wherein the azelastine or the pharmaceutically acceptable salt of azelastine is present in the pharmaceutical composition in an amount in the range of about 1 mg to about 6 mg.

Aspect 32 is the method of any of Aspects 25-31, wherein the azelastine or the pharmaceutically acceptable salt of azelastine is present in the pharmaceutical composition and is present in an amount in the range of up to about 8 mg, and the folic acid or folate, and/or salt, metabolite, or derivative thereof is present in the pharmaceutical composition and is present in an amount in the range of up to about 2 mg.

Aspect 33 is a pharmaceutical composition, comprising a first active agent, which is azelastine or a pharmaceutically acceptable salt of azelastine; and a second active agent, which is folic acid, folate, and/or salts, metabolites, or derivatives thereof; and one or more pharmaceutically acceptable excipients; wherein the second active agent is present in the pharmaceutical composition in a synergistically effective amount relative to the amount of the first active agent (i.e., the azelastine or pharmaceutically acceptable salt of azelastine and the folic acid, folate, and/or salts, metabolites, or derivatives thereof, are present in synergistically effective amounts).

Aspect 34 is the use of a pharmaceutical composition in the preparation of a medicament for treating a patient having one or more psychiatric disorder or symptom thereof, wherein the pharmaceutical composition comprises any composition of any of the above Aspects and/or the use involves any of the methods or any one or more method steps of the above Aspects.

Aspect 35 is a pharmaceutical composition for use in treating one or more psychiatric disorder or symptom, wherein the pharmaceutical comprises any composition of any of the above Aspects and/or the use involves any of the methods or any one or more method steps of the above Aspects.

DETAILED DESCRIPTION OF THE INVENTION

Through clinical practice, the inventors of the present invention found that a pharmaceutical composition with oral dosage forms comprising the active agents, a salt form of azelastine and folic acid, is suitable for treating patients suffering from psychiatric disorders or symptoms of psychiatric disorders such as one or more of major depressive disorder (MDD), generalized anxiety disorder (GAD), panic disorder, agitation, social anxiety disorder (SAD), mild chronic depression (MCD), obsessive-compulsive disorder (OCD), premenstrual dysphoric disorder (PDD), seasonal affective disorder (SAD), dysthymia, childhood enuresis, bipolar disorder, posttraumatic stress disorder (PSD or PTSD) and sleep disorders related to anxiety (SDRA).

The present application is related by subject matter to International Patent Application Nos. PCT/US19/27293, PCT/US19/29885, PCT/US19/33359, PCT/US20/34735, PCT/US20/39916, and PCT/US20/59846, each of which are hereby incorporated by reference herein in their entireties.

The detailed description provided below is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

Definitions

As used in the present specification, the following words and phrases are generally intended to have the meanings as set forth below, except to the extent that the context in which they are used indicates otherwise.

Psychiatric disorders and symptoms of psychiatric disorders can include but are not limited to major depressive disorder (MDD), generalized anxiety disorder (GAD), panic disorder, agitation, social anxiety disorder (SAD), mild chronic depression (MCD), obsessive-compulsive disorder (OCD), premenstrual dysphoric disorder (PDD), seasonal affective disorder (SAD), dysthymia, childhood enuresis, bipolar disorder, posttraumatic stress disorder (PSD or PTSD) and sleep disorders related to anxiety (SDRA).

As used herein, the term "folic acid" refers to folic acid, the synthetic form of folate, also called vitamin B9. In certain embodiments, folic acid also includes any pharmaceutically acceptable salt, such as calcium, sodium, potassium, magnesium, and various amines. In embodiments, folic acid includes pharmaceutically acceptable derivatives, such as esters, including mono- or di-esters. In other embodiments, folic acid can be replaced with folate or derivatives/metabolites of folate. Reference to the amounts and dosage ranges of folic acid, for example in the solid oral dosage forms, are to the amounts and dosage ranges of folate, folate derivatives and/or metabolites, or any pharmaceutically acceptable salt(s) thereof.

In embodiments, the one or more derivatives or biological metabolites of folate include dihydrofolate, tetrahydrofolate, levomefolic acid (levomefolate, 5-methyltetrahydrofolate (5-MTHF), L-methylfolate, L-5-methyltetrahydrofolate, or (6 S)-5-methyltetrahydrofolate), 5,10-methylenetetrahydrofolate, 5,10-methenyltetrahydrofolate, 5,10-formiminotetrahydrofolate, 5-formyltetrahydrofolate, and/or 10-formyltetrahydrofolate. In embodiments, the levomefolic acid is provided as a pharmaceutically acceptable salt, such as a calcium or magnesium salt.

As used herein, the term "azelastine" refers to azelastine free base, or 4-(p-Chlorobenzyl)-2-(hexahydro-1-methyl-1H-azepin-4-yl)-1-(2H)-phthalazinone. In certain embodiments, azelastine also includes any pharmaceutically acceptable salt, such as the hydrochloride or HCl salt. Preferably, in any embodiments of the invention as described herein, azelastine is in the form of its hydrochloride salt, as azelastine hydrochloride or azelastine HCl. More preferably, in any embodiment of the invention as described herein, reference to the amounts and dosage ranges of azelastine in the solid oral dosage forms are to the amounts and dosage ranges of azelastine hydrochloride, and reference to the amounts and dosage ranges of azelastine hydrochloride, for example in the solid oral dosage forms, are to the amounts and dosage ranges of azelastine or any pharmaceutically acceptable salt(s) thereof.

As used herein, "treating" or "treatment" means complete cure or incomplete cure, or it means that the symptoms of the underlying disease or associated conditions are at least affected, prevented, reduced, eliminated and/or delayed, and/or that one or more of the underlying cellular, physiological, or biochemical causes or mechanisms causing the symptoms are affected, prevented, reduced, delayed and/or eliminated. It is understood that reduced or delayed, as used in this context, means relative to the state of the untreated disease, including the molecular state of the untreated disease, not just the physiological state of the untreated disease.

The term "effective amount" refers to an amount that is sufficient to affect treatment, as defined below, when administered to an animal or mammal in need of such treatment. The therapeutically effective amount will vary depending upon the patient being treated, the weight and age of the patient, the severity of the disease condition, the manner of administration and the like, which can readily be determined by one of ordinary skill in the art. The pharmaceutical compositions may be administered in either single or multiple doses by oral administration. Administration may be by way of any one or more of capsule, tablet, gel, spray, drops, solution, suspensions, syrups, or the like.

The term "about" used herein in the context of quantitative measurements means the indicated amount ±10%. For example, with a ±10% range, "about 2 mg" can mean 1.8-2.2 mg.

The pharmaceutical compositions may be formulated for pharmaceutical use using methods known in the art, for example, Ansel's Pharmaceutical Dosage Forms and Drug Delivery Systems Tenth (Loyd Allen, 2013) and Handbook of Pharmaceutical Manufacturing Formulations (Volumes 1-6, Sarfaraz K. Niazi). Accordingly, incorporation of the active compounds and a controlled, or slow release matrix may be implemented.

Either fluid or solid unit dosage forms can be readily prepared for oral administration, for example, admixed with any one or more of conventional ingredients such as dicalcium phosphate, magnesium aluminum silicate, magnesium stearate, calcium sulfate, starch, talc, lactose, acacia, methyl cellulose and/or functionally similar materials as pharmaceutical excipients or carriers. A sustained release formulation may optionally be used. In older or incoherent subjects, sustained release formulations may even be preferred. Capsules may be formulated by mixing the pharmaceutical composition with a pharmaceutical diluent which is inert and inserting this mixture into a hard gelatin capsule having the appropriate size. If soft capsules are desired, a slurry of the pharmaceutical composition with an acceptable vegetable, light petroleum or other inert oil can be encapsulated by forming into a gelatin capsule.

Suspensions, syrups and elixirs may be used for oral administration or fluid unit dosage forms. A fluid preparation including oil may be used for oil soluble forms. A vegetable oil such as corn oil, peanut oil or a flower oil, for example, together with flavoring agents, sweeteners and any preservatives produces an acceptable fluid preparation. A surfactant may be added to water to form a syrup for fluid unit dosages. Hydro-alcoholic pharmaceutical preparations may be used having an acceptable sweetener, such as sugar, saccharin or other non-nutritive sweetener, and/or a biological sweetener and/or a flavoring agent, such as in the form of an elixir.

The solid oral dosage formulation of this disclosure means a form of tablets, caplets, bi-layer tablets, film-coated tablets, pills, capsules, or the like. Tablets in accordance with this disclosure can be prepared by any mixing and tableting techniques that are well known in the pharmaceutical formulation industry. In some examples, the dosage formulation is fabricated by direct compressing the respectively prepared sustained-release portion and the immediate-release portion by punches and dies fitted to a rotary tableting press, ejection or compression molding or granulation followed by compression.

The pharmaceutical compositions provided in accordance with the present disclosure can be typically administered orally. This disclosure therefore provides pharmaceutical compositions that comprise a solid dispersion comprising azelastine and folic acid as described herein and one or more pharmaceutically acceptable excipients or carriers including but not limited to, inert solid diluents and fillers, diluents, including sterile aqueous solution and various organic solvents, permeation enhancers, solubilizers, disintegrants, lubricants, binders, glidants, adjuvants, and combinations thereof. Such compositions are prepared in a manner well known in the pharmaceutical arts (see, e.g., Ansel's Pharmaceutical Dosage Forms and Drug Delivery Systems, Tenth (Loyd Allen, 2013) and Handbook of Pharmaceutical Manufacturing Formulations (Volumes 1-6, Sarfaraz K. Niazi)).

The pharmaceutical compositions may further comprise pharmaceutical excipients such as diluents, binders, fillers, glidants, disintegrants, lubricants, solubilizers, and combinations thereof. Some examples of suitable excipients are described herein. When the pharmaceutical compositions are formulated into tablets, tablets may be uncoated or may be coated by known techniques including microencapsulation to delay disintegration and absorption in the gastrointestinal tract and thereby provide a sustained action over a longer period. For example, a time delay material such as glyceryl monostearate or glyceryl distearate alone or with a wax may be employed. In embodiments, the pharmaceutical compositions are formulated as tablets, caplets, pills, or capsules capable of delaying disintegration until the pharmaceutical composition is in the gastrointestinal tract of a patient. In embodiments, delaying disintegration is achieved using a coating.

In embodiments, the pharmaceutical compositions can comprise a) about 1 mg-8 mg of azelastine HCl (or other salt thereof) and b) about 0.1 mg to 2 mg of folic acid or a) about 2 mg-6 mg of azelastine HCl (or other salt thereof) and b) about 0.1 mg to 0.8 mg of folic acid or folate, and/or salts, metabolites, or derivatives thereof or a) about 2 mg-4 mg of azelastine HCl (or other salt thereof) and b) about 0.2 mg to 0.4 mg of folic acid or folate, and/or salts, metabolites, or derivatives thereof, or any amount of azelastine or folic acid within these ranges. Additional embodiments include pharmaceutical compositions comprising a) above zero and about up to and including any of 1 mg, 2 mg, 3 mg, 4 mg, 5 mg, 6 mg, 7 mg or 8 mg azelastine, such as azelastine HCl or any salt of azelastine, or any amount within any of these ranges and b) above zero and about up to and including any of 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, or 2 mg folic acid or folate, and/or salts, metabolites, or derivatives thereof, or any amount within any of these ranges. For example, the compositions can comprise a) about 2 mg of azelastine HCl and b) about 0.4 mg of folic acid or folate, and/or salts, metabolites, or derivatives thereof. Further, for example, compositions of the invention can comprise azelastine or a pharmaceutically acceptable salt of azelastine present in an amount in the range of about 1 mg to about 8 mg and folic acid or folate, and/or salts, metabolites, or derivatives thereof in an amount in the range of about 0.1 mg to about 2 mg. In embodiments, the amount of azelastine HCl (or other salt thereof) present in the composition can be equal to, more than, or less than the amount of folic acid or folate, and/or salts, metabolites, or derivatives thereof present in the composition. In embodiments, azelastine is present in the pharmaceutical composition in an amount of at least 1 mg and folic acid or folate, and/or the salt, metabolite, or derivative thereof is present in an amount of at least 0.1 mg. In embodiments, the amount of azelastine HCl (and/or other salt thereof) present in the composition can be the same as, or 2 times as much, or 3 times as much, or 4, 5, 6, 7, 8, 9, 10, 15, 20, 25, 30, 35, 10, 15, or 50 times as much as the amount of folic acid or folate, and/or salt, metabolite, or derivative thereof present in the composition, or vice versa. Any one or more of the compositions of the invention can be used with any one or more the methods of the invention disclosed herein, or other methods of using the compositions.

In embodiments, the folic acid or folate, and/or salts, metabolites, or derivatives thereof, is present in the pharmaceutical composition in a synergistically effective amount relative to the amount of azelastine or the pharmaceutically acceptable salt of azelastine.

In embodiments, a pharmaceutical composition (e.g., comprising azelastine and folic acid) is used in the preparation of a medicament for treating a patient having one or more psychiatric disorder or symptom thereof. Such compositions can comprise a) about 1 mg-8 mg of azelastine (or salt thereof) and b) about 0.1 mg to 2 mg, such as about 0.1 mg to 1 mg, of folic acid or folate, and/or salts, metabolites, or derivatives thereof, or any of the amounts disclosed herein, or in synergistic amounts. Further, in embodiments, the pharmaceutical compositions can be for use in treating one or more psychiatric disorder or symptom, wherein the pharmaceutical comprises a) about 1 mg-8 mg of azelastine (or salt thereof) and b) about 0.1 mg to 2 mg, such as about 0.1 mg to 1 mg, of folic acid or folate, and/or salts, metabolites, or derivatives thereof, or any of the amounts disclosed herein, or in synergistic amounts.

It will be understood, that the amount of the pharmaceutical composition containing azelastine HCl and folic acid or folate, and/or salt, metabolite, or derivative thereof actually administered usually will be determined by a physician, in the light of the relevant circumstances, including the condition to be treated, the chosen route of administration, the actual compound administered and its relative activity, the age, weight and response of the individual patient, the severity of the patient's symptoms, and the like.

The pharmaceutical compositions, pharmaceutical dosage forms, and tablets containing azelastine, such as azelastine HCl, and folic acid or folate, and/or salts, metabolites, or derivatives thereof as described herein are administered to a patient suffering from one or more psychiatric disorders or symptoms such as major depressive disorder (MDD), generalized anxiety disorder (GAD), panic disorder, agitation, social anxiety disorder (SAD), mild chronic depression (MCD), obsessive-compulsive disorder (OCD), premenstrual dysphoric disorder (PDD), seasonal affective disorder (SAD), dysthymia, childhood enuresis, bipolar disorder, posttraumatic stress disorder (PSD or PTSD) and sleep disorders related to anxiety (SDRA), by administration (such as oral administration) once daily, twice daily, up to four times a day, once every other day, once a week, two times a week, three times a week, four times a week, or five times a week, or combinations thereof.

In embodiments, patients are administered the pharmaceutical composition(s) with a therapeutic effective daily dosage of azelastine (such as azelastine HCl) in the range of about 1 mg to about 8 mg and folic acid or folate, and/or salts, metabolites, or derivatives thereof in an amount in the range of about 0.1 mg to about 2 mg.

In embodiments, the pharmaceutical dosage forms and tablets of pharmaceutical compositions containing azelastine, such as azelastine HCl, and folic acid or folate, and/or salts, metabolites, or derivatives thereof as described herein are effective in reversing, reducing, alleviating, and/or treating one or more symptoms in patients with one or more psychiatric disorders or symptoms thereof, such as major depressive disorder (MDD), generalized anxiety disorder (GAD), panic disorder, agitation, social anxiety disorder (SAD), mild chronic depression (MCD), obsessive-compulsive disorder (OCD), premenstrual dysphoric disorder (PDD), seasonal affective disorder (SAD), dysthymia, childhood enuresis, bipolar disorder, posttraumatic stress disorder (PSD or PTSD) and sleep disorders related to anxiety (SDRA) in about 1-8 weeks, such as within 1, 2, 3, 4, 5, 6, 7, or 8 weeks, or any range in between.

In embodiments, the pharmaceutical composition is effective in reversing, reducing alleviating, and/or treating any one or more symptoms including, but not limited to, depression, anxiety, feelings of panic, agitation, delusions, hallucinations, irritability, insomnia, sleep disorder, aggression, etc.

The following Examples are illustrative and should not be interpreted to limit the scope of the claimed subject matter.

EXAMPLE 1

A 45-year-old female patient had MDD and panic disorder. She was treated with sertraline for 2 months and buspirone for 2 months but had no significant clinical improvement. When all of her symptoms worsened, she was given a composition of folic acid (0.19 mg) and azelastine (2 mg) once daily for 1 week, her symptoms started having a dramatic improvement. By 4 weeks of the treatment, she showed no panic disorder and her MDD was reduced by more than 80%. Because azelastine is approved for the treatment of allergic rhinitis and asthma, and the combination composition of azelastine and folic acid had never been expected to be used to treat patients with depression or anxiety, this dramatic clinical outcome which included a fast reduction of symptoms was unexpected. Although the inventors do not intend to be bound by this theory, it is believed that folic acid, through multiple signaling pathways, modulates the inflammatory response in microglia cells, shifting proinflammatory to anti-inflammatory responses, and those responses enhance and are synergistic with azelastine's anti-inflammatory action by its own function of suppressing release of cytokines, such as IL-1, IL-6, TNF-$\alpha$ and INF-$\alpha$, in the CNS system. This composition with two mechanisms of action of anti-inflammation would provide a new solution for treating psychiatric diseases which are incurable by other options, such traditional SSRIs, NSRIs, benzodiazepines, and the like alone.

EXAMPLE 2

A 55-year-old female patient was diagnosed with mild chronic depression and anxiety induced sleep disorder and was treated with citalopram and lorazepam for 3 months. Her symptoms were never improved to the level of her satisfaction. Then she was treated with a composition of folic acid (0.19 mg) and azelastine (2 mg) once daily. After 2 weeks, she exhibited dramatic clinical improvement and showed improvement of her depression by 80% and was satisfied with her sleeping quality. The inventors believe the hypothesis as explained in Example 1 above is applicable here as well. In this case, the composition of two mechanisms of action provided a new solution for treating her chronic depression and insomnia which could not be treated with other options, such traditional SSRIs, NSRIs, benzodiazepines, and the like alone.

REFERENCES

US Patent documents: 10,898,493, Jan. 26, 2021, Wang, et al.; 9,662,359, May 30, 2017 Vuckovic; 9,844,525, Dec. 19, 2017, Kiliaan, et al.; 9,504,712, Nov. 29, 2016, Kiliaan, et al.; 9,308,223, Apr. 12, 2016, Maewal; 8,440,243, Apr. 14, 2013, Maewal; 8,372,451, Feb. 12, 2013 Vuckovic; 8,362,078, Jan. 29, 2013, Kiliaan, et al; 7,888,391, Feb. 15, 2011, Kiliaan, et al.; 7,384,981, Jun. 10, 2008, Kiliaan, et al.; 6,200,607, Mar. 13, 2001, Bridgeman; 6,191,133, Feb. 20, 2001, Coppen.

A. F. Kolb and L. Petrie, "Folate deficiency enhances the inflammatory response of macrophages," Molecular Immunology, vol. 54, no. 2, pp. 164-172, 2013 6.

D. Feng, Y. Zhou, M. Xia, and J. Ma, "Folic acid inhibits lipopolysaccharide-induced inflammatory response in RAW264.7 macrophages by suppressing MAPKs and NF-$\kappa$B activation," Inflammation Research, vol. 60, no. 9, pp. 817-822, 2011.

Patrice B. Jones, et al. 2019. Folate and Inflammation—links between folate and features of inflammatory conditions. British Journal of Clinical Pharmacology, 18 (2019) 100104.

Reynolds E H., Folic acid, vitamin B12, and the nervous system: historical aspects. In: Botez M I, Reynolds E H, eds. Folic acid in neurology.

James P. Zacny, Judith A. Paice, and Dennis W. Coalson, 2012. Separate and combined psychopharmacological effects of folic acid and oxycodone in healthy volunteers, 2012 Aug. 1; 121(3): 271-282.

Bottiglieri T, et al., 2000. Homocysteine, folate, methylation and monoamine metabolism in depression. J Neurol Neurosurg Psychiatry 2000; 69:228-32.

Olga A. Balashova, et al., 2018. Folate action in nervous system development and disease. Dev Neurobiol. 2018 April; 78(4): 391-402.

Ruihua Hou et al., 2017, Peripheral inflammatory cytokines and immune balance in Generalized Anxiety Disorder: case-controlled study. Brain Behav Immun. 2017 May; 62:212-218.

Michelle Guignet et al., 2020, Persistent behavior deficits, neuroinflammation, and oxidative stress in a rat model of acute organophosphate intoxication, Vol 133, January 2020, 101131.

Chun-Hong Liu et al., 2019, Role of inflammation in depression relapse, Journal of Neuroinflammation (2019) 16:90

F. C. Bennett and A. V. Molofsky, 2019, The immune system and psychiatric disease: a basic science perspective, Clinical and Experimental Immunology, 197: 291-307.

Ruihua Hou and David S. Baldwin, 2012, A neuroimmunological perspective on anxiety disorders, Human Psychopharmacol Clin Exp. Vol 27: 6-11.

N Kappelmann, G Lewis, R Dantzer, P B Jones and G M Khandaker, 2018, Antidepressant activity of anti-cytokine treatment: a systematic review and meta-analysis of clinical trials of chronic inflammatory conditions, Molecular Psychiatry. Vol. 23, 335-313.

Conti, Pio et al., 2018, Impact of Mast Cells in Depression Disorder: Inhibitory Effect of IL-37 (New Frontiers). Immunol Res, vol. 66 (3), 323-331 June 2018.

Sung Ho Maeng and Heeok Hong, 2019, Inflammation as the Potential Basis in Depression. Int Neurourol J 2019; Vol 23(Suppl 2): S63-71.

Ole Köhler, et al. van Hoven P T, Kaufman A, Carr W W. Inflammation in Depression and the Potential for Anti-Inflammatory Treatment. Current Neuropharmacology, 2016, 11, 732-712.

Anzela Niraula et al. 2019, Interleukin-6 Induced by Social Stress Promotes a Unique Transcriptional Signature in the Monocytes That Facilitate Anxiety. Biol Psychiatry 85 (8), 679-689 2019 Apr. 15.

M Catena-Dell'Osso, et al, 2011, Inflammatory and Neurodegenerative Pathways in Depression: A New Avenue for Antidepressant Development? Curr Med Chem. 18 (2), 245-55.

S Georgin-Lavialle et al. 2016, Mast Cells' Involvement in Inflammation Pathways Linked to Depression: Evidence in Mastocytosis. Mol Psychiatry. 21 (11), 1511-1516 November 2016.

Sang Won Jeon, Yong Ku Kim, 2016, Detrimental effect of preservative in eye drops: Neuroinflammation and cytokine abnormality in major depression: Cause or consequence in that illness? World Journal of Psychiatry, 2016 Sep. 22; 6(3): 283-293.

Romain Troubat et al, 2020, Neuroinflammation and Depression: A Review. Eur J Neurosci. 2020 Mar. 9 DOI: 10.1111/ejn.14720.

Ja Wook Kooa, et al, 2010, Nuclear factor-κB is a critical mediator of stress impaired neurogenesis and depressive behavior. PNAS, Feb. 9, 2010, Vol. 107 (6) 2669-2674.

Patricia B Williams, Elizabeth Crandall and John D Sheppard, 2010, Azelastine hydrochloride, a dual-acting anti-inflammatory ophthalmic solution, for treatment of allergic conjunctivitis. Clinical Ophthalmology 2010:4 993-1001

Casale T. The interaction of azelastine with human lung histamine H1, beta, and muscarinic receptor-binding sites. J Allergy Clin Immunol. 1989; 83:771-776.

Hazama H, Nakajima T, Hisada T, Hamada E, Omata M, Kurachi Y. Effects of azelastine on membrane currents in tracheal smooth muscle cells isolated from the guinea-pig. Eur J Pharmacol. 1994; 259: 143-150.

Szelenyi I, Achterrath-Tuckermann U, Schmidt J, Minker E, Paegelow I, Werner H. Azelastine: A multifaceted drug for asthma therapy. Agents Actions Suppl. 1991; 34:295-311.

Galatowicz G, Ajayi Y, Stern M E, Calder V L. Ocular antiallergic compounds selectively inhibit human mast cell cytokines in vitro and conjunctival cell infiltration in vivo. Clin Exp Allergy. 2007; 37:1648-1656.

Ciprandi G, Pronzato C, Passalacqua G, et al. Topical azelastine reduces eosinophil activation and intercellular adhesion molecule-1 expression on nasal epithelial cells: An antiallergic activity. J Allergy Clin Immunol. 1996; 98(6 Pt 1):1088-1096.

Simons F E, Simons K J. Clinical pharmacology of new histamine H1 receptor antagonist. Clin Pharmacokinet. 1999; 36:329-352.

A Aiko Hatakeyama, 2008, Azelastine hydrochloride on behavioral and psychological symptoms and activities of daily living in dementia patients. Geriatr Gerontol Int 2008; 8: 59-61.

Duraisamy Kempuraj, et al. 2003, Azelastine Inhibits Secretion of IL-6, TNF-alpha and IL-8 as Well as NF-kappaB Activation and Intracellular Calcium Ion Levels in Normal Human Mast Cells. Int Arch Allergy Immunol. 132 (3), 231-9 Nov. 2003.

Kazunori Yoneda, et al. 1997, Suppression by Azelastine Hydrochloride of NF-κB Activation Involved in Generation of Cytokines and Nitric Oxide. Japanese Journal of Pharmacology, 73: 145-53.

Loyd Allen, Ansel's Pharmaceutical Dosage Forms and Drug Delivery Systems, Tenth (2013)

Sarfaraz K. Niazi, Handbook of Pharmaceutical Manufacturing Formulations Volumes 1-6.

The present invention has been described with reference to particular embodiments having various features. In light of the disclosure provided above, it will be apparent to those skilled in the art that various modifications and variations can be made in the practice of the present invention without departing from the scope or spirit of the invention. One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Any of the methods disclosed herein can be used with any of the compositions disclosed herein or with any other compositions. Likewise, any of the disclosed compositions can be used with any of the methods disclosed herein or with any other methods. Other embodiments of the invention will be apparent to those skilled in the art from consideration of the specification and practice of the invention.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

The invention claimed is:

1. A pharmaceutical composition, comprising:
   about 1 mg to about 8 mg azelastine or a pharmaceutically acceptable salt of azelastine;
   about 0.1 mg to about 2 mg folic acid or folate, and/or salts thereof;
   and one or more pharmaceutically acceptable excipients.

2. The pharmaceutical composition of claim 1, wherein the folic acid or folate, and/or salt thereof is present in the pharmaceutical composition in an amount in the range of about 0.1 mg to about 0.5 mg.

3. The pharmaceutical composition of claim 1, wherein the folic acid or folate, and/or salt thereof is present in the pharmaceutical composition in an amount in the range of about 0.1 mg to about 1 mg.

4. The pharmaceutical composition of claim 1, wherein:
   the azelastine or the pharmaceutically acceptable salt of azelastine is present in the pharmaceutical composition in an amount in the range of about 1 mg to about 4 mg; and
   the folic acid or folate, and/or salt thereof is present in the pharmaceutical composition in an amount in the range of about 0.1 mg to about 0.4 mg.

5. The pharmaceutical composition of claim 1, wherein the pharmaceutically acceptable salt of azelastine is azelastine hydrochloride.

6. The pharmaceutical composition of claim 2, wherein the pharmaceutically acceptable salt of azelastine is azelastine hydrochloride.

7. The pharmaceutical composition of claim 1, wherein the pharmaceutically acceptable salt of azelastine is azelastine hydrochloride and is present in an amount in the range of about 2-8 mg.

8. The pharmaceutical composition of claim 5, wherein the azelastine hydrochloride is present in an amount in the range of about 1 mg to about 4 mg.

9. The pharmaceutical composition of claim 1, wherein the pharmaceutical composition is formulated as an oral pharmaceutical dosage form.

10. The pharmaceutical composition of claim 9, wherein the oral pharmaceutical dosage form is a solid form or a liquid form.

11. A method of treating psychiatric disorders or symptoms thereof comprising:
    administering a pharmaceutical composition to a patient having a psychiatric disorder or having symptoms thereof;
    wherein the pharmaceutical composition comprises therapeutically effective amounts of azelastine, or a pharmaceutically acceptable salt of azelastine, and folic acid or folate, and/or salts, thereof;
    wherein the psychiatric disorders or symptoms are selected from major depressive disorders, generalized anxiety disorder, panic disorder, agitation, social anxiety disorder, mild chronic depression, premenstrual dysphoric disorder, obsessive-compulsive disorder, dysthymia, childhood enuresis, bipolar disorder, post-traumatic stress disorder, seasonal affective disorder, and anxiety-related sleep disorder.

12. The method of claim 11, wherein the pharmaceutical composition is administered once or twice a day, or once every 2 or 3 or 4 days to the patient in an oral solid or liquid form.

13. The method of claim 11, wherein the azelastine or the pharmaceutically acceptable salt of azelastine is present in the pharmaceutical composition in an amount in the range of about 1 mg to about 8 mg.

14. The method of claim 13, wherein the folic acid or folate, and/or salt thereof is present in the pharmaceutical composition in an amount in the range of about 0.1 mg to about 2 mg.

15. The method of claim 11, wherein the folic acid or folate, and/or salt thereof is present in the pharmaceutical composition in an amount in the range of about 0.1 mg to about 2 mg.

16. The method of claim 15, wherein the azelastine or the pharmaceutically acceptable salt of azelastine is present in the pharmaceutical composition in an amount in the range of about 1 mg to about 4 mg.

17. The method of claim 11, wherein:
    the azelastine or the pharmaceutically acceptable salt of azelastine is present in the pharmaceutical composition in an amount in the range of about 1 mg to about 4 mg; and
    the folic acid or folate, and/or salt, metabolite, or derivative thereof is present in the pharmaceutical composition in an amount in the range of about 0.1 mg to about 0.4 mg.

18. A pharmaceutical composition, comprising:
    a first active agent, which is azelastine or a pharmaceutically acceptable salt of azelastine;
    a second active agent, which is folic acid, folate, and/or salts thereof; and
    one or more pharmaceutically acceptable excipients;
    wherein the first and second active agents are present in synergistically effective amounts.

19. The pharmaceutical composition of claim 18, wherein:
    the first active agent is azelastine hydrochloride and is present in an amount in the range of about 1 mg to about 4 mg;
    the second active agent is folic acid or folate, and/or salts thereof, and is present in an amount in the range of about 0.1 mg to about 0.4 mg; and
    wherein the first active agent, the second active agent and the one or more pharmaceutically acceptable excipients are present together in an oral pharmaceutical dosage form.

* * * * *